United States Patent
Steglich

(10) Patent No.: US 6,498,943 B2
(45) Date of Patent: Dec. 24, 2002

(54) MULTI-POLAR ELECTRODE ARRANGEMENT

(75) Inventor: Carsten Steglich, Berlin (DE)

(73) Assignee: Biotronik Mess - und Therapiegerate GmbH & Co. Ingenieurbuero Berlin, Berlin (DE)

( * ) Notice: Subject to any disclaimer, the term of this patent is extended or adjusted under 35 U.S.C. 154(b) by 121 days.

(21) Appl. No.: 09/736,779

(22) Filed: Dec. 14, 2000

(65) Prior Publication Data
US 2001/0005792 A1 Jun. 28, 2001

(30) Foreign Application Priority Data
Dec. 23, 1999 (DE) .......................................... 199 63 603

(51) Int. Cl.⁷ .............................................. A61B 5/042
(52) U.S. Cl. ...................................... 600/374; 607/122
(58) Field of Search ................................. 600/374, 375; 607/119, 122, 126, 128

(56) References Cited

U.S. PATENT DOCUMENTS

| 5,029,585 A | | 7/1991 | Lieber | |
| 5,385,146 A | | 1/1995 | Goldreyer | |
| 5,394,880 A | | 3/1995 | Atlee | |
| 5,431,696 A | * | 7/1995 | Atlee, III | .................... 600/374 |
| 5,433,742 A | | 7/1995 | Willis | |
| 5,476,503 A | | 12/1995 | Yang | |
| 5,487,385 A | * | 1/1996 | Avitall | ......................... 600/374 |
| 5,797,842 A | * | 8/1998 | Pumares et al. | ............ 600/435 |
| 5,921,923 A | | 7/1999 | Kuck | |
| 5,941,834 A | | 8/1999 | Skladnev | |

FOREIGN PATENT DOCUMENTS

| EP | 0 823 264 A2 | 2/1998 |
| WO | WO 95/10979 A1 | 4/1995 |

OTHER PUBLICATIONS

Manoli, Yiannos and Mokwa, Wilfried, "Der intelligente Herzkatheter," Elektronik, p. 94–100, (Dec. 8, 1991).

* cited by examiner

Primary Examiner—Lee Cohen
(74) Attorney, Agent, or Firm—Hahn Loeser + Parks LLP; Stephen L. Grant

(57) ABSTRACT

A multipolar electrode arrangement having a plurality of electrodes (14, 14', 14") with an electrical feed line, wherein the electrodes (14, 14', 14") are connected to an electrode carrier (10) which is adapted to be insertable together with the electrodes (14, 14', 14") into the lumen of a catheter.

13 Claims, 2 Drawing Sheets

MULTI-POLAR ELECTRODE ARRANGEMENT

The invention concerns a multipolar electrode arrangement having a plurality of electrodes with an electrical feed line.

BACKGROUND OF THE ART

A particular area of use of multipolar electrode arrangements is the output of electrical signals to body tissue, in particular cardiac tissue, and picking up electrical signals from the heart. Contraction and relaxation of the cardiac muscles is controlled by electrical signals which pass through the cardiac tissue in an excitation front. Knowledge about signal propagation in the heart is an aspect of great significance, in terms of diagnosis and therapy of heart diseases. U.S. Pat. No. 5,921,923, to Kuck (Jul. 13, 1999), discloses a multipolar electrode arrangement in which the electrodes are arranged in such a way that not only the occurrence of events but in addition also the direction and speed of stimulus conduction can be detected.

For that purpose the poles are spatially arranged in relation to each other on the catheter in such a fashion that respective pairs thereof so-to-speak define a co-ordinate system. Other electrode arrangements are to be found in U.S. Pat. No. 5,385,146 to Goldreyer (Jan. 31, 1995) and U.S. Pat. No. 5,476,503 to Yang (Dec. 19, 1995).

SUMMARY OF THE INVENTION

That object is attained by an electrode arrangement of the kind set forth in the opening part of this specification, in which the electrodes are connected to an electrode carrier which is adapted to be insertable together with the electrodes into the lumen of a catheter.

An electrode arrangement of that kind permits simplified manufacture of any pole configurations in particular on a single lead electrophysiology catheter. In that respect the configuration of the electrodes is predetermined by the electrode carrier. The electrode carrier with the electrodes secured thereto can be pre-assembled and then inserted with electrical feed lines into a catheter tube.

A preferred electrode arrangement is one in which the electrode carrier is elastically deformable, more particularly preferably substantially in a first plane while it is substantially stiffer in a second plane which is perpendicular to the first plane. For that purpose the electrode carrier preferably includes a leaf spring element of preferably flat cross-sectional profile.

The leaf spring element is preferably of an electrically insulating nature and is preferably of a flat cross-sectional profile. In a preferred embodiment the electrode carrier and in particular the leaf spring element at least partially comprise a polymer. The electrode carrier can then be in the form of an injection molding in a particularly desirable fashion.

The advantages of an electrode arrangement with such an electrode carrier are pertinent in particular when the electrode carrier is connected at its distal end to a control means which is guided longitudinally slidably along the electrode carrier relative thereto so that deflection of the electrode carrier can be effected at the distal end thereof by longitudinal displacement of the control means relative to the electrode carrier. It is possible in that way to provide an electrophysiology catheter which can be targetedly and specifically deflected in cavities such as for example the atrium or ventricle of a heart and guided into a defined direction in order to be able to pick up signals at defined locations in the heart. For that purpose the catheter tip can be provided with marking means which make it possible to locate the catheter tip from outside the body by means of imaging processes.

Preferably, the electrode arrangement includes a catheter having a lumen which is adapted to receive the electrode carrier, wherein the catheter has openings which extend from the lumen and which are of such an arrangement and configuration that the electrodes connected to the electrode carrier can pick up electrical signals outside the catheter. In a preferred alternative configuration, the openings can be disposed in the peripheral surface of the catheter and in particular of a catheter tube, more specifically in such a way that a corresponding opening is provided for each individual electrode. Alternatively however the electrode carrier can also be designed in such a way that as a whole it projects out of a central opening at the distal end of the catheter or catheter tube.

A further preferred electrode arrangement is one in which the electrodes are arranged in mutually displaced relationship in the longitudinal and peripheral directions of the catheter in such a way as to afford at least one electrode matrix which makes it possible to determine the direction and speed of a signal from the time displacement with which the signal reaches various ones of the electrodes. In that respect, an adequate spacing not only in respect of the center points of the surfaces of the individual electrodes but between the electrode surfaces is advantageous in terms of determining the speed of the stimulus conduction.

In the above-mentioned electrode arrangement an electrode matrix preferably includes at least three electrodes, wherein the center points of the surfaces of the electrodes of an electrode matrix are preferably arranged at the corners of notional triangles or quadrangles.

As an alternative to the electrodes being made from metal, which affords the advantage of the high level of conductivity of metal, a particularly preferred electrode arrangement is one in which the electrodes include conductive plastic material.

In an advantageous embodiment, such an electrode arrangement makes it possible to arrange the electrodes in depressions in a non-conductive base material, in particular the insulating leaf spring element. The depressions can be produced for example with a high degree of precision by means of a laser beam so that even small microstructures can be produced. The non-conductive base material can be a component part of the electrode carrier.

In principle electrodes of conductive plastic material are known from U.S. Pat. specifications Nos. 5,433,742 and 5,029,585.

BRIEF DESCRIPTION OF THE DRAWINGS

The invention will now be described in greater detail by means of embodiments with reference to the Figures in which.

DETAILED DESCRIPTION OF THE INVENTION

Figure 1:
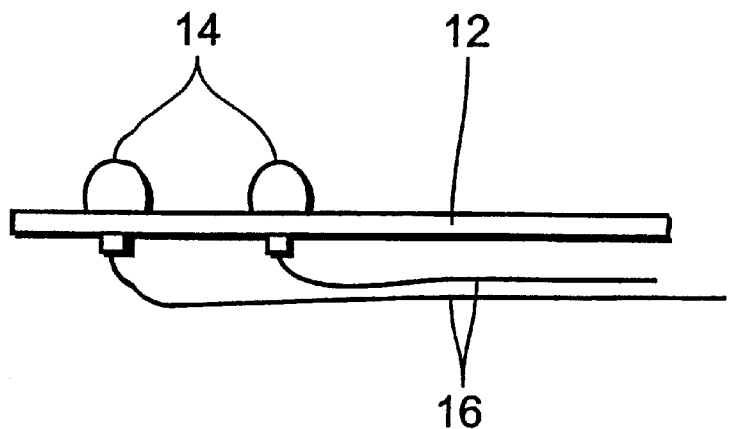
FIG. 1 is a side view of an electrode carrier together with electrodes and feed lines.

FIG. 1 shows an electrode carrier 10 whose essential component is an insulating leaf spring element 12. Secured to the insulating leaf spring element 12 are two electrodes 14 by the electrodes 14 being glued or riveted to the leaf spring element 12. A respective electrical feed line 16 is associated with each electrode 14. The electrodes 14 comprise platinum, iridium or electrical conductive plastic material.

Figure 2:
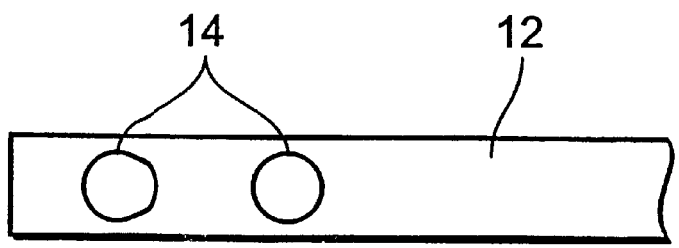
FIG. 2 is a plan view of the electrode carrier of FIG. 1.

FIG. 2 is a plan view of the electrode carrier of FIG. 1 and therewith the arrangement of the electrodes 14 on the insulating leaf spring element 12. The electrodes 14 are arranged at a spacing from each other on the longitudinal axis of the insulating leaf spring element 12. The spacing of the electrodes 14 from each other means that a signal with a component of propagation in the longitudinal direction of the leaf spring element reaches the one electrode 14 prior to the other. In that way it is possible to determine the speed component of signal propagation in the longitudinal direction of the leaf spring element from the time delay with which the signal is detected by the two electrodes 14.

Figure 3:
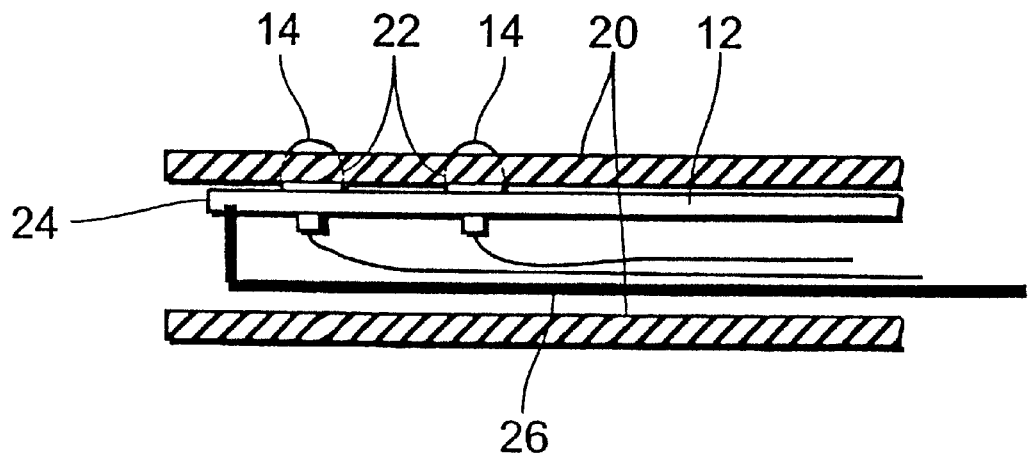
FIG. 3 shows the electrode carrier of FIGS. 1 and 2, inserted into a single-lumen tube of an electrophysiology catheter.

In FIG. 3, the electrode carrier 10 shown in FIGS. 1 and 2 is inserted into a single-lumen tube 20 of an electrophysiology catheter. The tube has two openings 22 which are provided to receive the electrodes 14 so that they project outwardly from the lumen of the tube in order to be able to pick up electrical signals outside the tube.

In addition, secured to the distal end 24 of the leaf spring element 12 is a control mechanism 26 which can be formed for example by a wire which, with the exception of the location of its fixing to the distal end 24 of the leaf spring element 12, is displaceable relative to the leaf spring element 12 in the longitudinal direction thereof. In that way, the electrophysiology catheter can be specifically and targetedly deflected laterally in the region of the leaf spring element 12 in the manner of per se known controllable guide wires.

The electrode carrier design implemented in FIGS. 1 through 3 permits a simple arrangement of multipolar electrodes. A great advantage lies in simple handling in terms of production. The electrode carrier together with the electrodes 14 can be completely pre-assembled as a unit and then fitted into the single-lumen tube 20. The insulating leaf spring element 12 is of a rectangular cross-sectional shape which, in a plane extending through the longitudinal axis of the leaf spring element 12, provides for a high level of lateral stability while it permits elastic deflection of the leaf spring element 12 in a plane which is perpendicular to the first plane.

Figure 4:
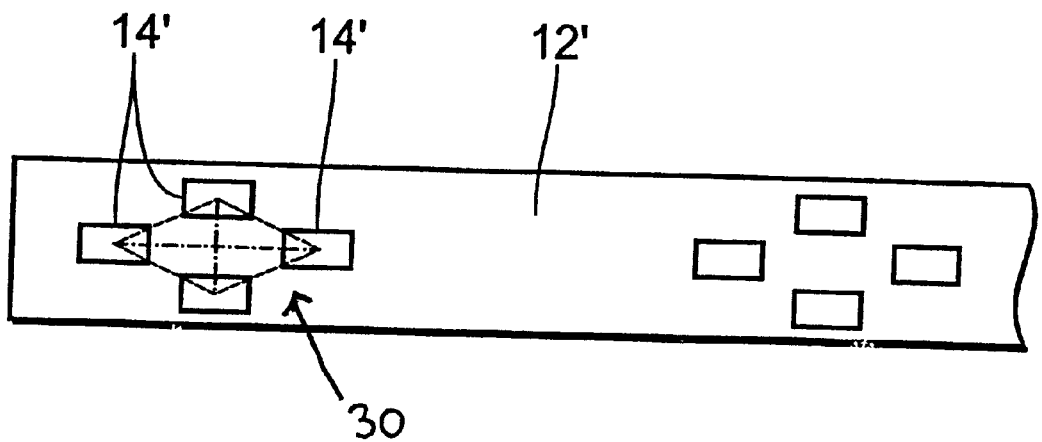
FIG. 4 is a view similar to FIG. 2 of an electrode carrier with an alternative electrode arrangement.
Figure 5:
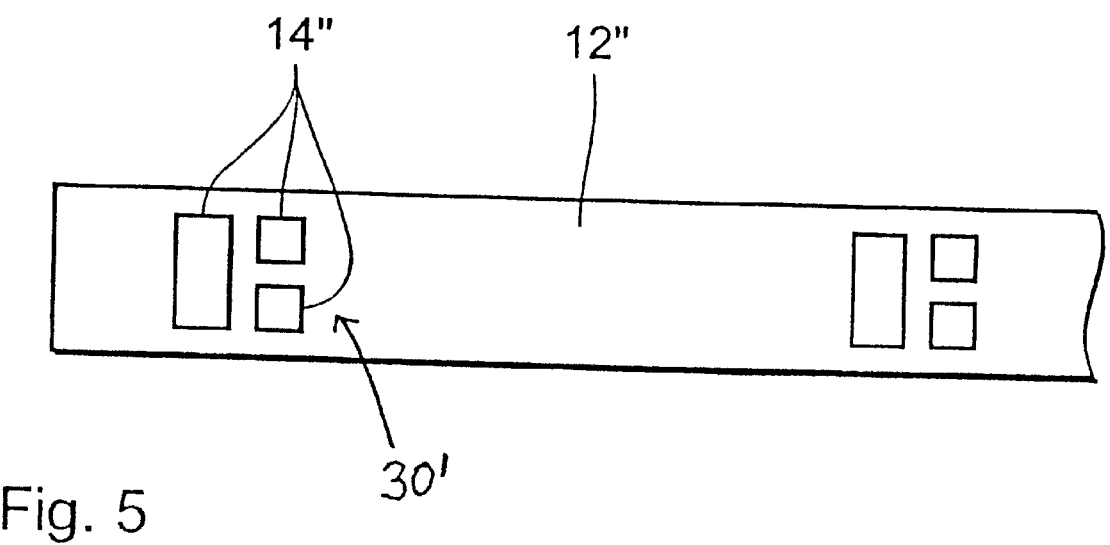
FIG. 5 shows an electrode carrier with a second alternative electrode arrangement.

FIGS. 4 and 5 each show respective alternative electrode arrangements. In FIG. 4 a total of eight electrodes 14' are arranged on the leaf spring element 12'. Four electrodes 14' in each case are combined to form a respective electrode matrix 30. The electrodes 14' of an electrode matrix are arranged at a spacing from each other in such a way that the center points of their surfaces lie at the corners of a notional quadrangle. That notional quadrangle is of mirror-image symmetrical configuration in relation to those two axes which connect the respectively non-adjacent corners of the quadrangle. Those two axes moreover are perpendicular to each other and one of those axes extends in the direction of the longitudinal axis of the spring element 12. The notional quadrangle is shown in broken line in FIG. 4 and the two axes connecting the corners are shown in dash-dotted lines.

In FIG. 5 the two electrode matrices 30' are each formed by three electrodes 14". The three electrodes 14" of an electrode matrix 30' are not all of the same surface area, like the electrodes 14' of FIG. 4. On the contrary, one of the electrodes 14" is of twice the surface area as the other two electrodes 14" of the same electrode matrix 30'. The two smaller electrodes 14" are arranged in side-by-side relationship at both sides of the longitudinal axis, shown in broken line, of the leaf spring element 12". The third larger electrode 14" is arranged adjacent to the two smaller electrodes 14" in the longitudinal direction of the leaf spring element 12".

The electrode arrangements in FIGS. 4 and 5 have a series of common features: the individual electrodes 14', 14" of an electrode matrix 30, 30' are at a spacing from each other which is of sufficient size so that an advancing signal reaches one or two of the electrodes of the electrode matrix earlier than the other electrodes. Both the direction of propagation and also the speed of propagation of the signal can be determined from the time displacement with which a signal reaches the individual electrodes of an electrode matrix 30, and from the arrangement of the electrodes within the electrode matrix 30, 30'.

In addition, each of the electrode arrangements shown has two electrode matrices 30, 30' which are at a substantially greater spacing from each other in the longitudinal direction of the leaf spring element 12', 12", than the spacing of the electrodes 14', 14" of an electrode matrix 30, 30' from each other.

The electrodes 14' and 14" of the electrode arrangements shown in FIGS. 4 and 5 are formed by depressions in the insulating leaf spring element 12', 12", which are filled with conductive plastic material. To produce such electrodes, firstly for example a laser beam is used to produce the depressions in the insulating leaf spring element 12 or 12'. This can be done with a very high degree of accuracy. Those depressions are then filled with conductive plastic material. The electrodes produced in that way involve a high level of accuracy. At the same time the manner of manufacture involved is particularly simple. This kind of electrode configuration can therefore also be used in a different context and is not limited to the uses in connection with the described electrode carrier.

What is claimed is:

1. A multipolar electrode arrangement for insertion into a lumen of a catheter, the arrangement comprising:
   a plurality of electrodes, each said electrode provided with an electrical feed line; and
   an elastically deformable electrode carrier, connected to each electrode, the electrode carrier having a distal end which is adapted to be insertable together with the electrodes;
   wherein the electrode carrier is elastically deformable substantially in a first plane while it is substantially stiffer in a second plane which is perpendicular to the first plane; and
   wherein the electrode carrier further comprises an insulating leaf spring element.

2. The electrode arrangement as set forth in claim 1, characterized in that the leaf spring element has a flat cross-sectional profile.

3. The electrode arrangement of claims 1, wherein the electrode carrier at least partially comprises a polymeric material.

4. The electrode arrangement of claim 1, wherein the plurality of electrodes are arranged in mutually displaced relationship on the electrode carrier in such a way as to define at least one electrode matrix which makes it possible to determine the direction and speed of a signal to be picked up, from the time displacement with which the signal reaches various ones of the electrodes or to define the direction and speed of a signal to be outputted.

5. The electrode arrangement as set forth in claim 4 characterized in that each said electrode matrix comprises at least three electrodes.

6. The electrode arrangement of claim 4 wherein each said electrode of the plurality of electrodes has a surface with a center point thereof such that the respective center points in the at least one electrode matrix are arranged to define the corners of a triangle.

7. The electrode arrangement of claim 4 wherein each said electrode of the plurality of electrodes has a surface with a center point thereof such that the respective center points in the at least one electrode matrix are arranged to define the corners of a quadrangle.

8. The electrode arrangement of claim 1, wherein at least one of the said plurality of electrodes comprises conductive plastic material.

9. The electrode arrangement as set forth in claim 8 characterized in that at least one of the plurality of electrodes is formed in a depression of a non-conductive portion of the electrode carrier.

10. The electrode arrangement of claim 1, further comprising a control means connected at a distal end thereof to the distal end of the electrode carrier and longitudinally displaceable therealong, such that deflection of the distal end of the electrode carrier can be implemented by longitudinal displacement of the control means relative thereto.

11. A multipolar electrode arrangement, comprising:
   a cathether having a lumen;
   an electrode carrier, inserted into the lumen of the catheter; and
   a plurality of electrodes, each said electrode provided with an electrical feed line, wherein each said electrode is connected to the electrode carrier;
   wherein the catheter has a plurality of openings which extend from the lumen such that the number and configuration of the openings corresponds to the number and configuration of the electrodes, with each of the plurality of electrodes extending through the corresponding opening to pick up or output electrical signals outside the catheter.

12. A multipolar electrode arrangement for insertion into a lumen of a catheter, the arrangement comprising:
   a plurality of electrodes, each said electrode provided with an electrical feed line, and an electrode carrier, connected to each said electrode, the electrode carrier having a distal end which is adapted to be insertable together with the electrodes;
   wherein the plurality of electrodes are arranged in mutually displaced relationship on the electrode carrier so as to define at least one electrode matrix which makes it possible to determine the direction and speed of a signal to be picked up, from the time displacement with which the signal reaches various ones of the electrodes or to define the direction and speed of a signal to be outputted; and
   wherein each said electrode of the plurality of electrodes has a surface with a center point thereof such that the respective center points in the at least one electrode matrix are arranged to define the corners of a triangle.

13. A multipolar electrode arrangement for insertion into a lumen of a catheter, the arrangement comprising:
   a plurality of electrodes, each said electrode provided with an electrical feed line, and
   an electrode carrier, connected to each said electrode, the electrode carrier having a distal end which is adapted to be insertable together with the electrodes;
   wherein the plurality of electrodes are arranged in mutually displaced relationship on the electrode carrier so as to define at least one electrode matrix which makes it possible to determine the direction and speed of a signal to be picked up, from the time displacement with which the signal reaches various ones of the electrodes or to define the direction and speed of a signal to be outputted; and
   wherein each said electrode of the plurality of electrodes has a surface with a center point thereof such that the respective center points in the at least one electrode matrix are arranged to define the corners of a quadrangle.

* * * * *